United States Patent [19]
Lerch

[11] Patent Number: 5,837,139
[45] Date of Patent: Nov. 17, 1998

[54] FLUID COLLECTING AND DIVIDING APPARATUS

[76] Inventor: Andrea M. Lerch, 2512 Rimrock Dr., Colorado Springs, Colo. 80915

[21] Appl. No.: 839,504

[22] Filed: Apr. 14, 1997

[51] Int. Cl.⁶ .................................................. B01D 29/085
[52] U.S. Cl. .......................... 210/474; 210/474; 206/569; 422/278; 220/86.1; 141/237; 141/242
[58] Field of Search ..................................... 210/474, 477; 206/569; 422/61, 102, 278; 220/86.1; 141/18, 35, 234, 237, 242

[56] References Cited

U.S. PATENT DOCUMENTS

| | | |
|---|---|---|
| 1,524,419 | 1/1925 | Berry . |
| 3,520,412 | 7/1970 | Frank et al. . |
| 3,776,235 | 12/1973 | Ratcliffe et al. ......................... 128/295 |
| 3,927,701 | 12/1975 | Lederer ................................. 220/144.5 |
| 4,683,911 | 8/1987 | Mayes . |
| 4,701,101 | 10/1987 | Sapoff ..................................... 222/229 |
| 4,981,144 | 1/1991 | Carels, Jr. . |
| 5,326,473 | 7/1994 | Lescombes et al. ..................... 210/474 |
| 5,409,117 | 4/1995 | Meador ................................... 206/569 |
| 5,498,395 | 3/1996 | Moore, Jr. et al. . |

*Primary Examiner*—W. L. Walker
*Attorney, Agent, or Firm*—Richard W. Hanes

[57] ABSTRACT

A fluid collecting and separating vessel comprising side walls forming a lateral enclosure, a bottom member attached to the lower perimeter of the side walls and including a pair of spaced apart fluid discharge openings and a pair of attached funnels, each having a hollow substantially cone shaped upper portion surrounding one of the openings and a walled drainage tube depending from the point of the cone, where the base of the cone is a closed plane figure congruent with one half of the lower perimeter of the side walls.

7 Claims, 3 Drawing Sheets

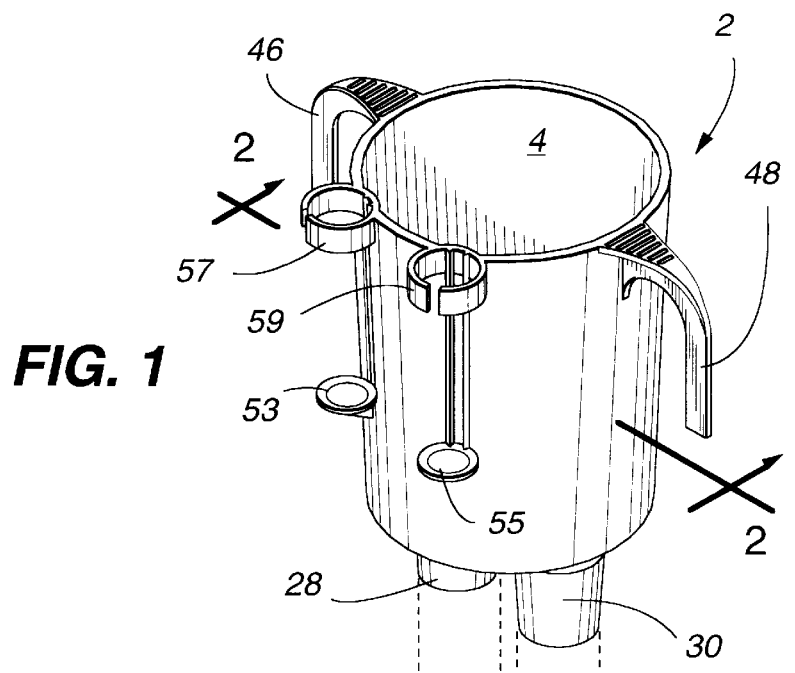
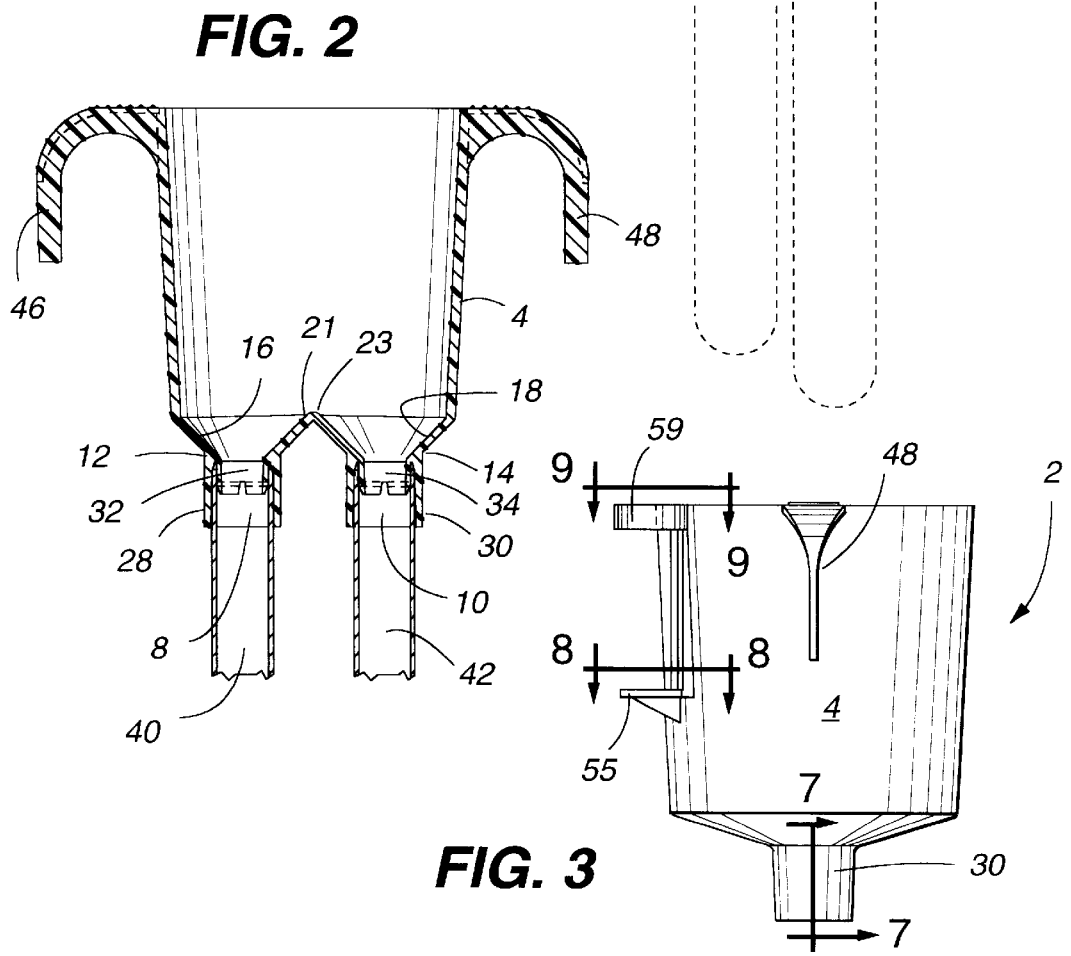

FLUID COLLECTING AND DIVIDING APPARATUS

The present invention relates generally to a vessel for the collection of a fluid that is divided into two portions and then diverted into separate containers.

BACKGROUND OF THE INVENTION

Body fluids, such as blood or urine, are collected and analyzed during many medical procedures. Frequently, a plurality of tests is required to be run on the same specimen. It is therefore convenient, and sometimes even necessary, to employ a collection device which will not only separate the collected fluid into separate portions for testing, but also divert it into appropriate containers, such as test tubes. In tests of urine, for example, a sterile container is necessary for a culture test, while an unsterile container is suitable for a urinalysis. When collecting blood samples from that portion of an umbilical cord still attached to the placenta after the birth of a baby, it is necessary to have an anti-coagulant added to one sample, whereas, such an addition is not required for another.

The prior art has seen several devices intended for similar purposes, however none of these apparatus serve well for the especially important function of collecting and dividing blood collected from the umbilical cord. U.S. Pat. No. 5,498,395 discloses a liquid collection and separation device that is the most similar to the present invention of those known to the inventor hereof. This patented device provides a bowl-like collector having a pair of spaced apart depending spouts that each fit into the mouth of a test tube that is held and supported by a stand resting on a flat surface, such as a laboratory bench or table. Such a collection and separating device has several drawbacks that are overcome by the present invention. For example, inserting the fluid discharge down spouts into the mouths of the test tubes does not provide a close fit between the spouts' outer surfaces and the interior of the tubes' sidewalls, thus creating the possibility of leakage at the connection site and contamination of the specimen. Second, relying on a desk stand to support the test tubes severely limits the use of the device to a laboratory table or bench top. In such a setting, a specimen initially collected in another container must be transferred into the bowl-shaped separating container, creating spillage and additional contamination possibilities and adding one more item to the chore of biohazard waste disposal.

Other devices for the same or similar purpose are seen in U.S. Pat. Nos. 4,981,144, 4,683,911 and 5,415,665. None of these apparatus contain the novel features of the present invention.

OBJECTS OF THE INVENTION

It is therefore the principal object of the present invention to provide a fluid collecting and separating vessel that will gather and separate the fluid at the original collection site and, at the same time, divert the separated fluid into test tubes which are retained by the collection vessel itself.

A second object of the present invention is to provide a plurality of fluid discharge ports in a collection vessel that will each hold the mouth of a test tube in sealing engagement to eliminate leakage and contamination at the coupling of the test tube and vessel.

Another object of the invention is to provide a collection vessel that will drain and separate all of the collected fluid into the test tubes attached to the vessel, without retaining any of the fluid.

A still further object of the invention is to provide a unitary collection and fluid-separating device that may be hand-held during the collection process.

Other and still further objects, features and advantages of the invention will become apparent upon a reading of the following description of a preferred form of the invention, taken in conjunction with the attached drawings.

DESCRIPTION OF THE DRAWINGS

FIG. 1 is a perspective view of the collection vessel of the present invention with attachable test tubes shown in phantom.

FIG. 2 is a cross sectional view taken along lines 2—2 of FIG. 1.

FIG. 3 is a right side view of the collection vessel.

DETAILED DESCRIPTION OF THE INVENTION

Figure 4:
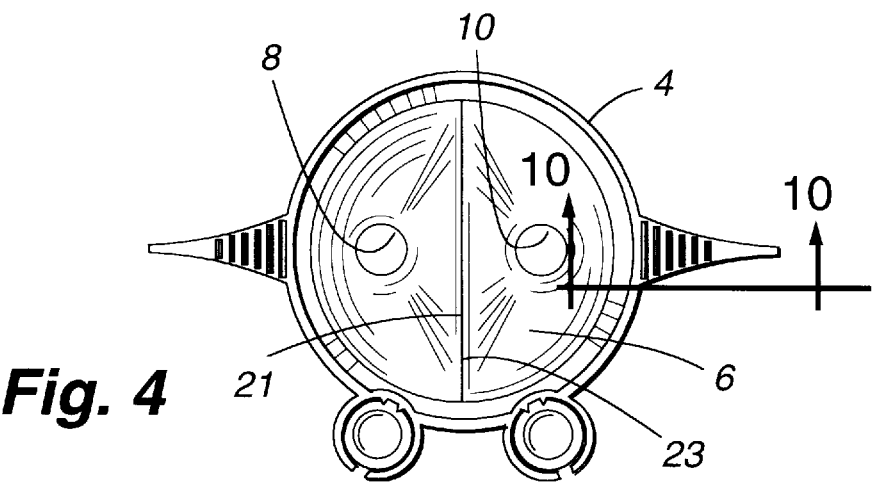
FIG. 4 is a top view of the collection vessel.
Figure 5:
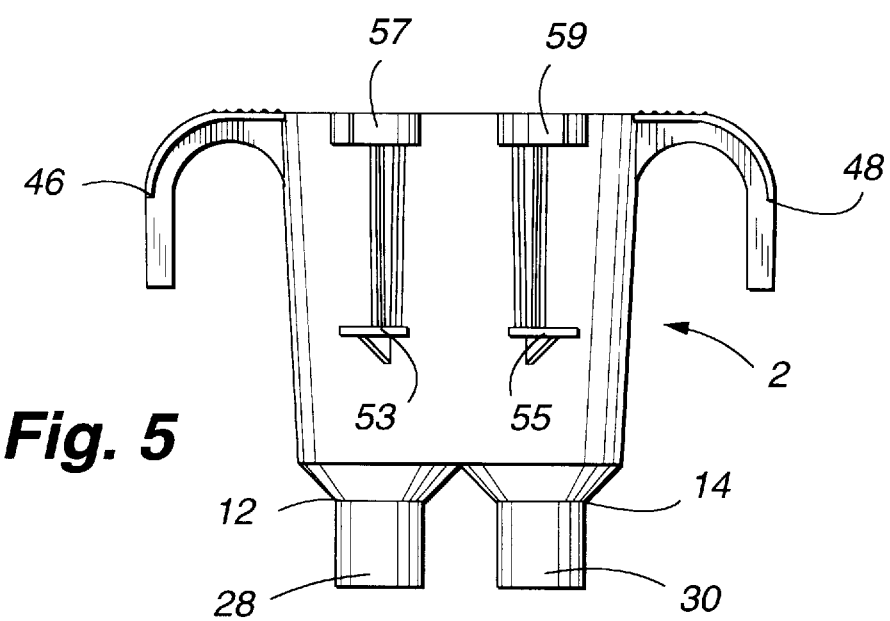
FIG. 5 is a front view of the vessel.
Figure 6:
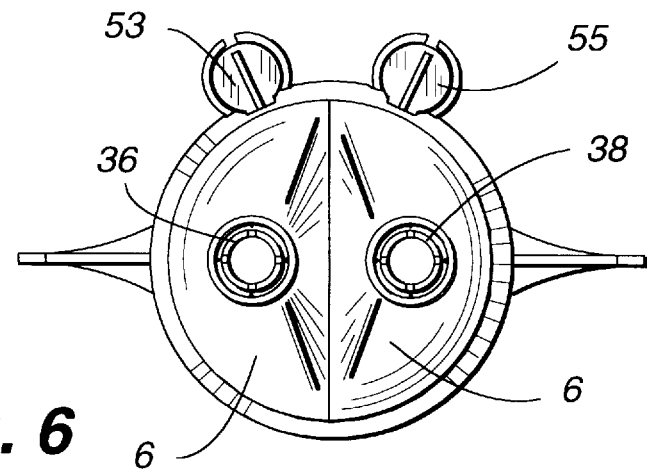
FIG. 6 is a bottom view of the vessel.
Figure 7:
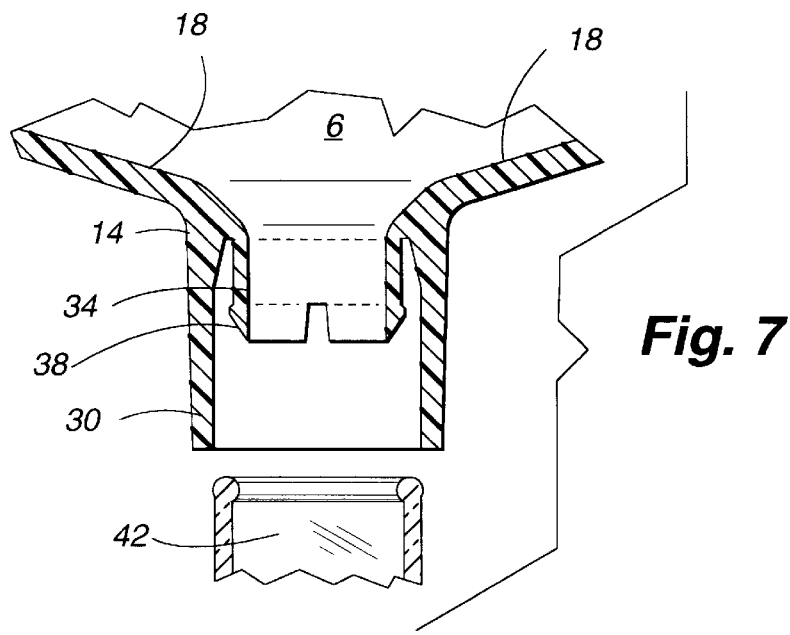
FIG. 7 is an enlarged fragmentary cross sectional view taken along lines 7—7 of FIG. 3.
Figure 8:
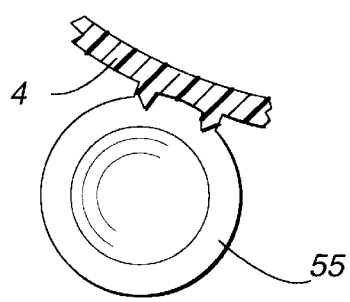
FIG. 8 is an enlarged fragmentary cross sectional view taken along lines 8—8 of FIG. 3.
Figure 9:
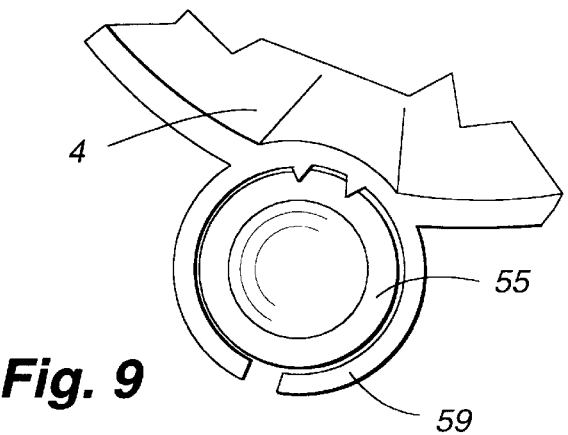
FIG. 9 is an enlarged fragmentary view taken from lines 9—9 of FIG. 3.
Figure 10:
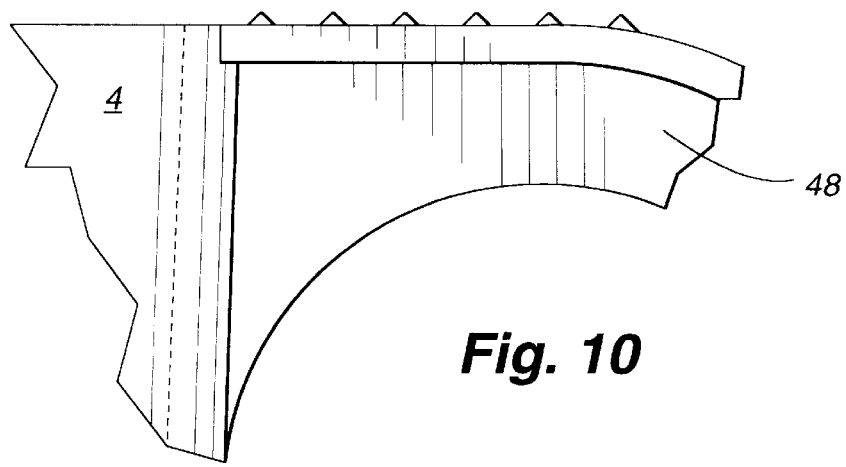
FIG. 10 is an enlarged fragmentary cross sectional view taken along lines 10—10 of FIG. 4.

The preferred form of the invention comprises a circular cup-shaped vessel 2, having upwardly diverging sidewalls 4 that form the upper enclosure for the vessel. The vessel could take other shapes. The bottom 6 of the vessel contains two spaced apart discharge ports 8 and 10. Each of the discharge ports is formed as the interior of a funnel 12 and 14. A typical symmetrical funnel comprises a right circular cone having a tube depending from the point of the cone. However, the cones, or beveled surfaces, 16 and 18 of the funnels 12 and 14, are not identical about all axes of the respective funnels. The cones are symmetric about the vertical axes, but they are not identical in their front and side views, as seen in the contrasting FIGS. 3 and 5. Accordingly, for purposes of defining this invention, the inclined surfaces 16 and 18 may be referred to as substantially cone-shaped. Each of the substantially shaped cone portions of the funnels 12 and 14 has a base, which, if the beveled surfaces defined a right circular cone, would be a circle. In the preferred embodiment, the base of the substantially cone-shaped portion of each funnel is semi-circular. The two flat, or straight line, sides 21 and 23 of the respective funnels are joined to form the diameter of the bottom of the cup-shaped vessel 2.

Tubes 28 and 30 depend from the so-called point of the substantial cones 16 and 18. Inside the tubes 28 and 30, and sealingly attached to the circular outlet of each of the substantial cones, are nipples 32 and 34. The distal end of each of the nipples includes a radially projecting circumferential lip 36 and 38 containing a plurality of notches so as to render the distal end and the mid-section of the nipple compressible, since the preferred material of the vessel is plastic. The outside surface of the nipples is spaced apart from the inside surface of the tube in which the nipple is disposed.

The above-described construction of the nipple and the drain tube of the respective funnels is adapted to receive the side walls of the mouth of test tubes 40 and 42. When pushed into place, the test tube walls fit tightly between the interior wall of the tubes 28 and 30 and the compressible outside surface of the nipples 32 and 34. It has been found that the outside diameter of most test tubes is a closely controlled dimension, while the inside diameter is not. This novel construction of the compressible nipple inside the funnel tube accommodates the variations of inside diameter dimension and provides a tight fit between the test tube and the funnel tube. This tight fit serves to implement several of the objects of the invention. Leakage and associated contamination are eliminated. The test tubes are carried and completely supported by the collection vessel. No other support is required.

The collection and separating vessel 2, together with the attached containment test tubes 40 and 42, can be held with one hand of the person collecting the specimen, while the other hand can be used to hold the umbilical cord and direct the blood discharge therefrom into the vessel 2. Projecting handles 46 and 48 serve to assist in holding and controlling the vessel 2.

An added feature to the preferred embodiment includes a means 50 for holding the test tubes after they are filled with fluid so as to facilitate the capping the test tubes. Molded integrally with the vessel sides is a spaced pair of projecting shelves 53 and 55. These shelves each support a test tube. The upper portion of the test tube is stabilized by a partial ring 57 and 59 projecting from the side of the vessel directly above the respective supporting shelf. The rings, or other stabilizing means, can be partial rings, as shown in the preferred form, full rings or some other appropriately shaped enclosure.

I claim:

1. A fluid collecting vessel comprising, side walls having upper and lower perimeters and forming an enclosure, a bottom member attached to the side walls and including, a pair of spaced apart fluid discharge openings, a pair of funnels, each having a hollow substantially cone shaped upper portion surrounding one of the openings and a walled drainage tube depending from the point of the cone, where the base of the cone is a closed plane figure congruent with one half of the lower perimeter of the side walls.

2. The vessel of claim 1 and further including, a tubular nipple projecting from around each of the said openings into the interior of the respective drainage tube and spaced apart from the walls of the tube.

3. The combination of claim 2 where the nipple is diametrically compressible.

4. The vessel of claim 1 where each of the closed planes comprise a common straight-line portion which divides the bottom symmetrically between the openings.

5. A fluid collecting vessel comprising, side walls having upper and lower perimeters and forming an enclosure, a bottom member attached to the side walls and including, a pair of spaced apart openings, a pair of funnels, each having a hollow substantially cone shaped upper portion surrounding one of the openings and a walled tube depending from the point of the cone and where the base of the cone is a closed plane figure congruent with one half of the lower perimeter of the side walls and where each of the closed planes comprise a common straight line portion which divides the bottom symmetrically between the openings.

6. A fluid collecting vessel comprising, side walls having upper and lower perimeters and forming an enclosure, a bottom member attached to the side walls and including, a pair of spaced apart fluid discharge openings, a pair of funnels, each having a hollow substantially cone shaped upper portion surrounding one of the openings and a walled drainage tube depending from the point of the cone, where the base of the cone is a closed plane figure congruent with one half of the lower perimeter of the side walls, a tubular nipple projecting from around each of the said openings into the interior of the respective drainage tube and spaced apart from the walls of the tube, where the nipple is diametrically compressible, and where the nipple includes a radially projecting circumferential lip.

7. A fluid collecting vessel comprising, side walls having upper and lower perimeters and forming an enclosure, a bottom member attached to the side walls and including, a pair of spaced apart openings, a pair of funnels, each having a hollow substantially cone shaped, upper portion surrounding one of the openings and a walled tube depending from the point of the cone and where the base of the cone is a closed plane figure congruent with one half of the lower perimeter of the side walls and where each of the closed planes comprise a common straight line portion which divides the bottom symmetrically between the openings, a pair of shelf like supports projecting from the exterior of the side walls, and a pair of ring means attached to the exterior of the side walls in a position superimposed over the respective shelf like supports.

* * * * *